(12) United States Patent
Schöb

(10) Patent No.: US 6,181,040 B1
(45) Date of Patent: Jan. 30, 2001

(54) MAGNETICALLY JOURNALLED ROTATIONAL ARRANGEMENT

(75) Inventor: Reto Schöb, Volketswil (CH)

(73) Assignees: Sulzer Electronics AG, Winterhur (CH); Lust Antriebstechnik GmbH, Lahnau (DE)

( * ) Notice: Under 35 U.S.C. 154(b), the term of this patent shall be extended for 0 days.

(21) Appl. No.: 09/128,047

(22) Filed: Aug. 3, 1998

(30) Foreign Application Priority Data

Aug. 25, 1997 (EP) .................................................. 97810595

(51) Int. Cl.$^7$ ............................ H02K 7/09; H02K 49/00
(52) U.S. Cl. ........................................... 310/90.5; 310/103
(58) Field of Search .......................... 310/87, 90.5, 103; 417/422.12, 423.14

(56) References Cited

U.S. PATENT DOCUMENTS

| | | | |
|---|---|---|---|
| 5,350,283 | 9/1994 | Nazazeki | 310/90.5 |
| 5,424,595 | * | 6/1995 | Preston et al. ........................ 310/90.5 |
| 5,720,160 | * | 2/1998 | Traxler et al. ........................ 310/90.5 |
| 5,725,357 | * | 3/1998 | Nakazeki et al. ................ 417/423.12 |
| 5,856,719 | * | 1/1999 | De Armas ............................ 310/103 |
| 5,947,703 | * | 9/1999 | Nojiri et al. ..................... 417/423.14 |

FOREIGN PATENT DOCUMENTS

| | | |
|---|---|---|
| 0130541A1 | 1/1985 | (EP) . |
| 0501427A1 | 9/1992 | (EP) . |
| 1054336 | * 1/1967 | (GB) .................................. 310/103 |
| WO-A-96/19034 | 12/1995 | (WO) . |
| WO 96/19034 | 6/1996 | (WO) . |
| WO 96/31934 | 10/1996 | (WO) . |
| WO 97/15978 | 5/1997 | (WO) . |

\* cited by examiner

*Primary Examiner*—Clayton LaBalle
(74) *Attorney, Agent, or Firm*—Townsend and Townsend and Crew LLP

(57) ABSTRACT

A magnetically journalled rotational arrangement comprises a bearing stator and a rotor, with the bearing stator being magnetically coupled to the rotor and producing a magnetic journalling of the rotor. The bearing stator is rotatably journalled. Furthermore, a rotary drive which is associated with the bearing stator is provided, with a rotation of the bearing stator producing a rotation of the rotor via the magnetic coupling of the stator to the rotor.

29 Claims, 9 Drawing Sheets

MAGNETICALLY JOURNALLED ROTATIONAL ARRANGEMENT

BACKGROUND OF THE INVENTION

1. Field Of The Invention

The invention relates to a magnetically journalled rotational arrangement. The invention also relates to forwarding apparatuses, carrier apparatuses, blowers and stirrers with a rotational arrangement of this kind.

2. Description Of The Prior Art

Magnetically journalled rotational arrangements are used today in numerous fields of application, in particular, however, where mechanically journalled rotational arrangements have considerable disadvantages, thus e.g. in stirrers or forwarding apparatuses for highly pure or biological liquids such as, for example, blood. Magnetically journalled rotational arrangements are also used in applications such as clean room blowers where high demands are placed on cleanliness and no contamination, such as is caused e.g. by gases which can escape from the lubricants of mechanical bearings, may be tolerated. In these applications, both a journalling of the rotor (which can be designed e.g. as the vaned wheel of a pump) and a rotational movement of the same must be possible.

A pump is proposed in U.S. Pat. No. 5,350,283 in which a magnetically journalled rotational arrangement is used. The pump described there has a rotor (e.g. a vaned wheel) which is arranged in the interior of the pump and which is magnetically journalled in the axial direction. The rotor has permanent magnets pointing in the axial direction at its one side for this purpose. A rotor is arranged outside the pump housing and is likewise provided with correspondingly arranged permanent magnets. The permanent magnets of the rotor, which is arranged outside the pump housing, are likewise arranged to point in the axial direction and indeed in such a manner that they come to lie opposite to the permanent magnets of the rotor. On the other side the rotor is equipped with a U-shaped soft iron. Corresponding U-shaped control magnets which produce the actual journalling of the rotor are arranged outside the pump housing, opposite to the U-shaped soft iron. The control magnets have a permanent magnet for the production of a bias magnetization and control windings which are arranged at fixed positions on the pump housing.

SUMMARY OF THE INVENTION

The object of the invention is to provide a magnetically journalled rotational arrangement by means of which a magnetic journalling and a rotation of the rotor can be produced at the same time. The magnetically journalled rotational arrangement should be as uncomplicated and inexpensive as possible and should, in particular, also permit the initially named uses.

DETAILED DESCRIPTION OF THE PREFERRED EXEMPLARY EMBODIMENTS

Figure 1:
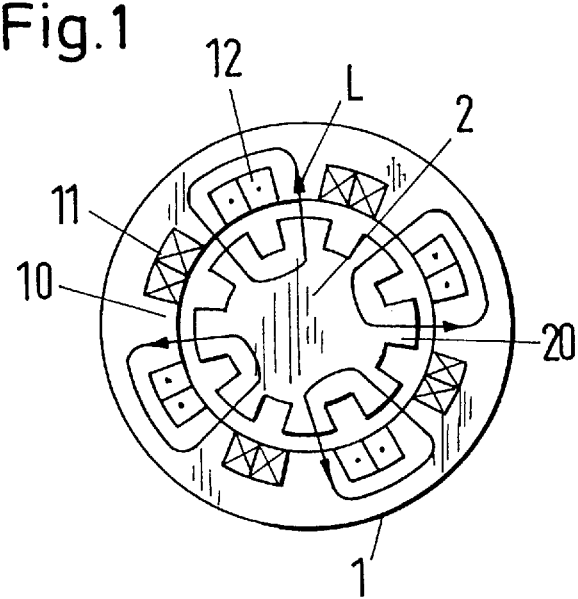
FIG. 1 is a sketch of the principles of an exemplary embodiment of the rotational arrangement in accordance with the invention for the explanation of the method of operation.

In the sketch of the principle of an exemplary embodiment of the rotational arrangement (here, a radial magnetic bearing) in accordance with the invention illustrated in FIG. 1, one recognizes a bearing stator 1 and a rotor 2. The bearing stator 1 has teeth 10 and the rotor 2 has corresponding teeth 20, with the teeth 10 and 20 of the bearing stator 1 and of the rotor 2 being arranged to point in the direction of one another. The number of the teeth 10 of the bearing stator 1 and of the teeth 20 of the rotor 2 are in agreement. Grooves 11 are located between the teeth 10 of the bearing stator 1; corresponding grooves 21 are located between the teeth 20 of the rotor 2. Windings 12 are wound around the individual teeth 10 of the bearing stator 1. During operation, these windings are flowed through by currents e.g. in the illustrated manner, so that the magnetic circuits indicated by the arrows L are formed. For the sake of better clarity, only a few of these magnetic circuits are representatively indicated in FIG. 1.

The rotor 2 is uniformly attracted to all sides in the radial direction by the bearing stator 1 in the desired position, through which the magnetic journalling of the rotor 2 is effected. The bearing stator 1 and the rotor 2 are thus magnetically coupled. If now the bearing stator 1 is rotated, then the rotor 2 also rotates synchronously with the stator as a result of the reluctance forces (the reluctance forces always act in such a manner that the teeth have a tendency to lie opposite one another). It is self explanatory that the greater the magnetic flux is, the greater the reluctance forces will be. The reluctance forces, however, act not only in a stabilizing manner with respect to a rotation of the rotor 2 relative to the bearing stator 1; they also produce a stabilization of the rotor 2 in the axial direction or with respect to a possible tilting of the rotor about the two tilt axes. Thus whereas an active stabilization of two degrees of freedom (namely the stabilization with respect to a displacement of the rotor in two directions in the bearing plane) takes place, a passive stabilization of the other four degrees of freedom (namely the stabilization of the rotor with respect to the two tilt axes, the axial stabilization of the rotor and the stabilization against a rotation relative to the stator in the bearing plane) takes place through reluctance forces.

In the exemplary embodiment of the rotational arrangement in accordance with the invention shown in FIG. 2 one again recognizes the bearing stator 1 and the rotor 2 as well as a container 3 which is arranged between the bearing stator 1 and the rotor 2, and which consists e.g. of plastic or also of aluminum, in general of a non ferromagnetic material and in the inner space of which the rotor 2 is arranged. The bearing stator 1 in turn is connected to a bracket bar 4 which can likewise consist of a non ferromagnetic material, e.g. of plastic (but can also consist of a magnetically poorly conducting metal). The bracket bar 4 is rotatably journalled in two bearings B and can be rotationally driven by means of a motor M. Furthermore, one also recognizes an electronic control system 5 schematically. This is supplied with electrical energy by means of an electrical energy source G via slip rings S (that is, through mechanical contact) and via (non-illustrated) leads; alternatively, a non contact inductive energy transfer is also possible (see e.g. FIG. 23).

If now the bracket bar 4 is rotationally driven by means of the motor M then the bearing stator 1 is also thereby rotated. The rotor 2 follows—as already explained—this rotational movement of the bearing stator 1 as a result of the reluctance forces. In this manner, for example, a stirrer, a pump, in particular a pump for highly pure or biological liquids, especially for blood, can be driven. Other applications of a rotational arrangement of this kind are e.g. a blower for clean room applications or a carrier apparatus for wafers. This will be gone into in further detail below.

Figure 3:
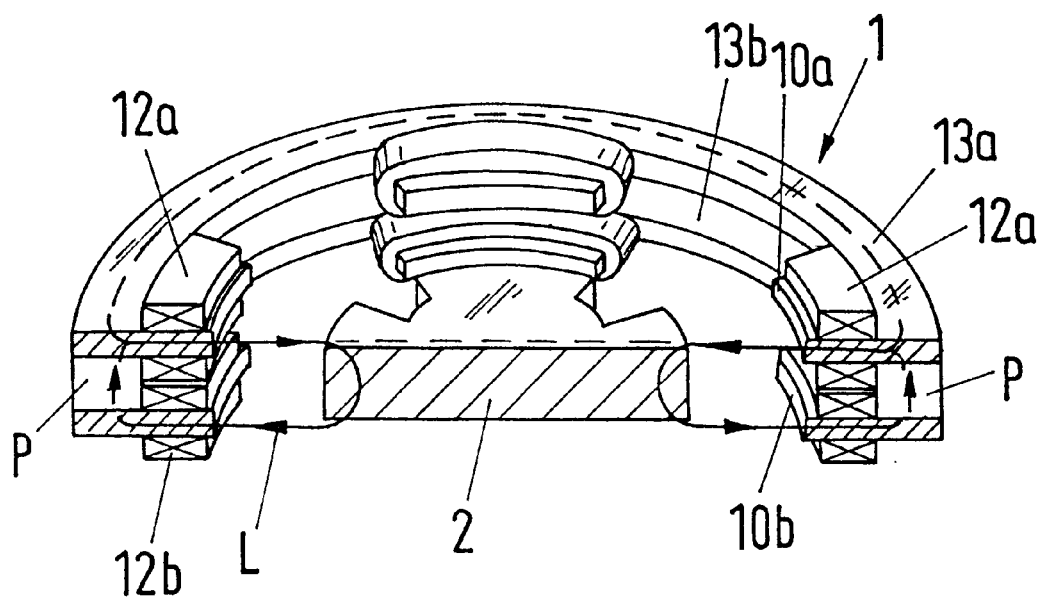
FIG. 3 shows an exemplary embodiment of the bearing stator and of the rotor.

FIG. 3 shows an exemplary embodiment of the bearing stator 1 and of the rotor 2 in an enlarged illustration. One recognizes that the bearing stator 1 here comprises two stator rings 13a and 13b, of which the teeth 10a and 10b in each case project inwardly in the direction of the rotor 2. Permanent magnets P which are magnetized in the axial direction are arranged between the two stator rings 13a and 13b, which consist of a ferromagnetic material (e.g. of iron). Furthermore, one recognizes the windings 12a and 12b, respectively, which are wound around the respective teeth 10a and 10b, respectively, and which are formed here as purely control windings in order to be able to guarantee the equilibrium of the magnetic forces at all times.

The magnetic flux produced by the permanent magnets P extends, departing from the permanent magnets P, through the tooth 10a of the upper stator ring 13a, across the air gap between the bearing stator 1 and the rotor 2, through the rotor 2, and back again across the air gap over the tooth 10b of the lower stator ring 13b to the permanent magnet P so that the magnetic circuit L is closed. If now the rotor 2 is deflected radially (that is, in the bearing plane) from its desired position, then a control flux CF can be produced with the help of the control windings 12a and 12b with the help of which the rotor 2 can be moved back into its desired position. The path of the control flux CF is indicated in the upper stator ring 13a by a broken line (analogous considerations hold for the lower stator ring 13b). The control flux CF extends in the plane of the stator ring 13a. In the region of the teeth it is superimposed on the permanent magnetic flux produced by the permanent magnets so that the latter can be either reinforced or weakened depending on the direction in which the rotor 2 must be moved in order to return to its desired position. In this exemplary embodiment, the rotor 2 is manufactured of a ferromagnetic material, e.g. of iron, but has no special features so that it can be manufactured economically. This is advantageous, in particular, if the rotor 2 must be formed as a throw away part or must be recycled after use as a result of its field of application. Moreover, the bearing force in the desired position of the rotor 2 is practically completely supplied by the permanent magnets P (magnetic bias) in this exemplary embodiment, through which, on the one hand, the consumption of electrical energy is kept low (and thereby only low heat losses develop), but a high flux and thereby also large reluctance forces are produced at the same time.

Figure 4:
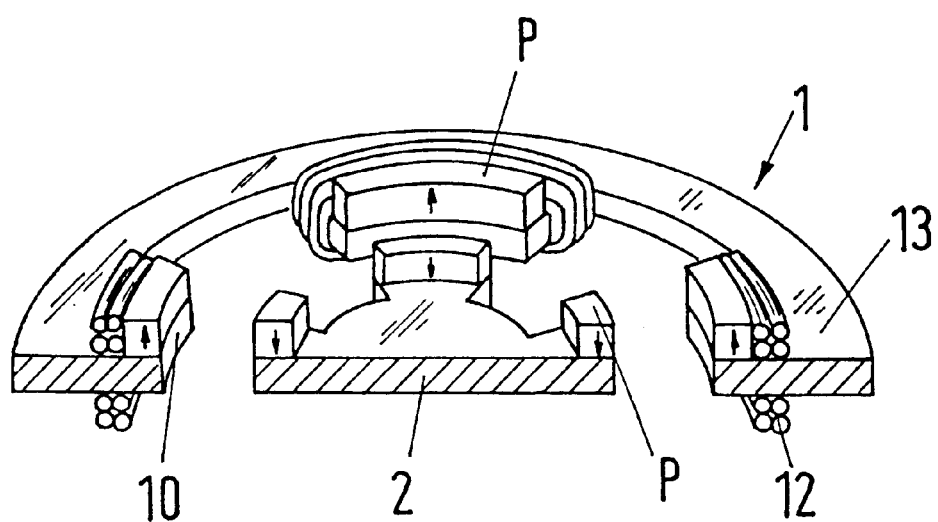
FIG. 4 shows a further exemplary embodiment of the bearing stator and of the rotor.

The exemplary embodiment of the bearing stator 1 and of the rotor 2 shown in FIG. 4 differs from the exemplary embodiment shown in FIG. 3 essentially wherein only one stator ring 13 is provided in the exemplary embodiment shown in FIG. 4, and wherein permanent magnets P which are magnetized in the axial direction are provided not only in the bearing stator 1, but also at the rotor 2. Since the air gap to be bridged in the exemplary embodiment of FIG. 4 is greater than that of the exemplary embodiment of FIG. 3 (since the back closure for the permanent magnetic flux takes place via the air, with the flux first being directed in the axial direction), permanent magnets P are also provided on the rotor 2. This arrangement is thus in so far somewhat more complicated and expensive as permanent magnets P are likewise provided in the rotor 2. In return the arrangement is even smaller with respect to its axial measurement than in the exemplary embodiment of FIG. 3. In addition, tilting of the rotor 2 can be even better stabilized.

It is self evident that permanent magnets P can also be provided at the rotor 2 in the exemplary embodiment of FIG. 3, e.g. the rotor 2 can comprise two ferromagnetic discs, between which correspondingly magnetized permanent magnets P can be arranged. The reluctance forces are thereby increased even further, or a larger air gap can be tolerated between the bearing stator 1 and the rotor 2 without the ability to function suffering therefrom. Admittedly, the rotor 2 is a bit more complicated and expensive—due to the additional permanent magnets P. Alternatively, the dimensioning can remain the same as shown in FIG. 3, in which case the equipment of the rotor 2 with permanent magnets P has the result that even greater reluctance forces can be produced in this manner.

Figure 5:
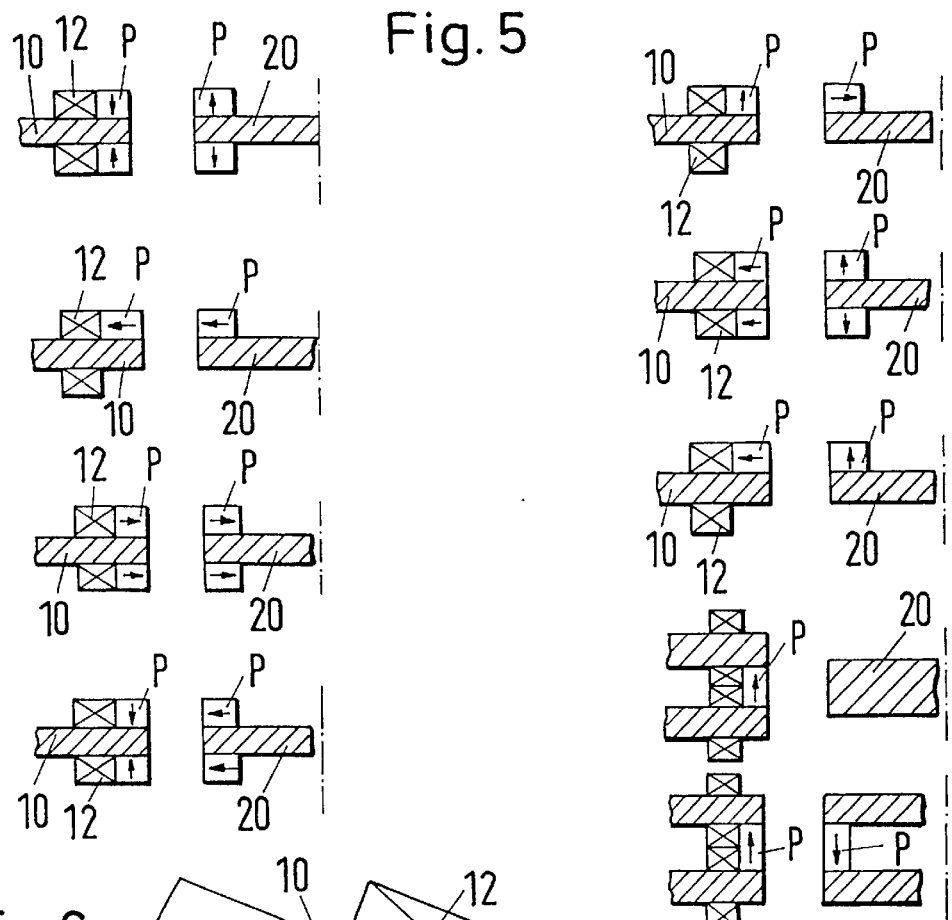
FIG. 5 shows different combinations of the arrangement of permanent magnets on the bearing stator and on the rotor.

Further possible examples of arrangements of permanent magnets P on the bearing stator 1 and the rotor 2, in particular, permanent magnets P which are magnetized in the radial direction and combinations of axially magnetized and radially magnetized permanent magnets P, are illustrated in FIG. 5. These are, beginning in the left column from top to bottom and then in the right column from top to bottom, in order:

i) axially magnetized permanent magnets P arranged on both sides of the rotor 2 (at the teeth 20) and correspondingly in the stator 1 (at the teeth 10);

ii) radially magnetized permanent magnets P arranged on one side of the rotor 2 (e.g. at the top of the rotor) and correspondingly in the stator 1;

iii) radially magnetized permanent magnets P arranged on both sides of the rotor 2 and correspondingly in the stator 1;

iv) axially magnetized permanent magnets P arranged on both sides of the rotor 2 and at the same time radially magnetized permanent magnets P arranged correspondingly in the stator 1;

v) radially magnetized permanent magnets P arranged on one side of the rotor 2 (e.g. at the top of the rotor) and axially magnetized permanent magnets P arranged correspondingly in the stator 1;

vi) axially magnetized permanent magnets P arranged on both sides of the rotor and radially magnetized permanent magnets P arranged correspondingly in the stator 1;

vii) axially magnetized permanent magnets P arranged at one side of the rotor 2 (e.g. on the rotor) and radially magnetized permanent magnets P arranged correspondingly in the stator 1;

viii) no permanent magnets on the rotor 2, axially magnetized permanent magnets P and two control windings in the stator 1;

ix) axially magnetized permanent magnets P in the rotor 2 and in the stator 1, two control windings in the stator 1.

It is self explanatory that the magnetization directions shown in the individual examples in FIG. 5 can also be oriented in reverse.

Figure 6:
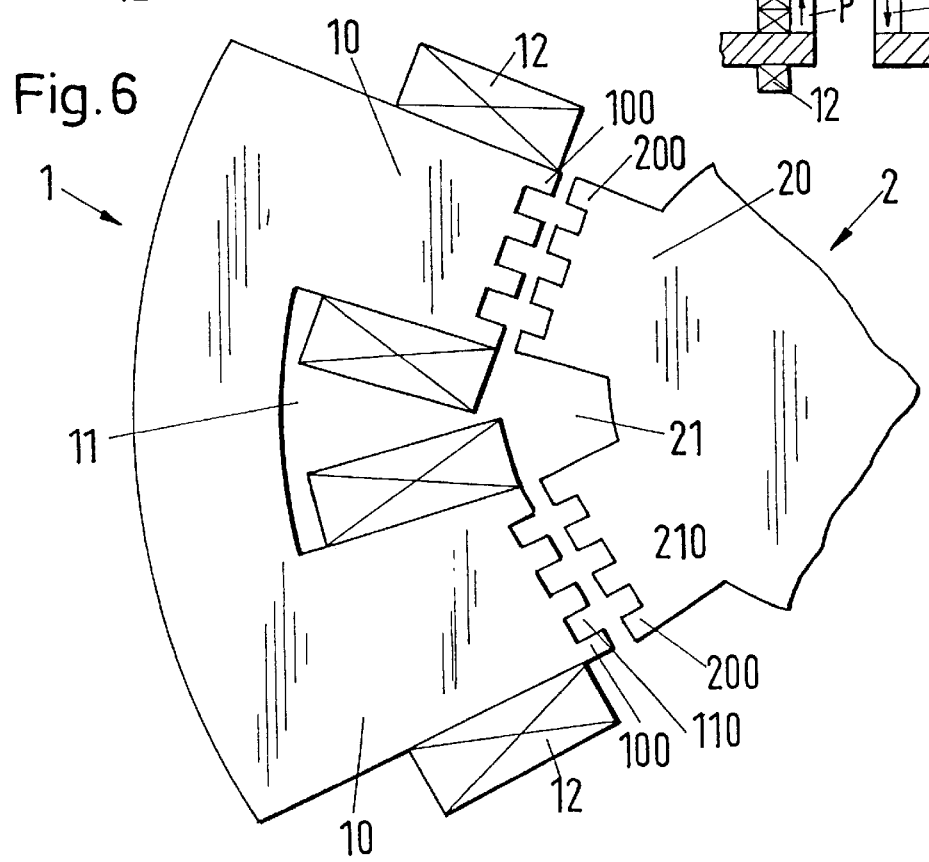
FIG. 6 is a section of mutually oppositely lying teeth of the bearing stator and of the rotor with grooves on the surfaces which face one another.

In FIG. 6, one recognizes a section of mutually oppositely lying teeth 10 and 20 of the bearing stator 1 and of the rotor 2. The surfaces of the teeth 10 and 20 facing one another in turn have mutually oppositely lying teeth 100 and 200 and grooves 110 and 210 lying therebetween, the number and spatial arrangement of which are in agreement. In this manner, the reluctance forces can yet again be increased, through which also the maximum torque which can be transmitted can yet again be increased.

Figure 7:
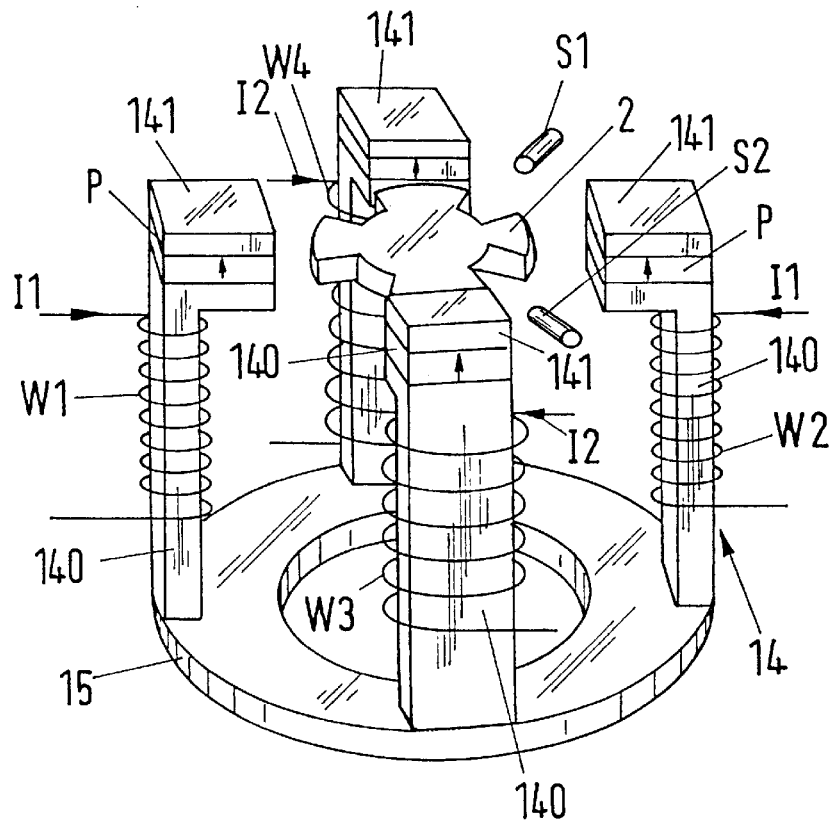
FIG. 7 shows a further exemplary embodiment of a rotational arrangement in accordance with the invention.

FIG. 7 shows a further exemplary embodiment of a rotational arrangement in accordance with the invention, a so-called temple arrangement. In this temple arrangement, the bearing stator comprises a ferromagnetic base disc or base ring 15. L-shaped winding cores 14 stand off from this base ring 15 in the axial direction, the longer limbs 140 of which point in the axial direction and the shorter limbs 141 of which point towards one another in the radial direction and thus practically form the teeth of the bearing stator. Control windings 12 are provided about the longer limbs 140, whereas in the region of the shorter limbs 141 axially magnetized permanent magnets P are provided here which practically completely produce the bearing forces (bias magnetization) in the desired position of the rotor. Oppositely lying windings W1, W2 and W3, W4, respectively, have an opposite winding sense and can be connected in series and, where appropriate, flowed through by the control current I1 and I2, respectively, in order to be able to correct a deviation of the rotor from the desired position. The windings W1, W2 and W3, W4, respectively, can also be connected in parallel. A deviation of the rotor 2 from its desired position is determined by means of the sensors S1, S2 and communicated to the electronic control system already mentioned earlier (not shown here). The electronic control system then feeds corresponding control currents I1, I2 into the windings W1, W2 and W3, W4, respectively, so that the rotor 2 is again moved back to its desired position. Due to the flux produced by the permanent magnets P and due to the opposed winding senses of the windings W1, W2 and W3, W4, respectively, an increase in the flux at one side of a winding and thereby a greater attraction force on the rotor 2 is always produced at the same time as a reduction of the flux and thereby a reduction of the force at the other side of the winding (due to the opposing senses of the windings). The L-shaped winding cores 14 and the base ring 15 can be laminated, i.e. consist of a plurality of layers of metal sheets in order to reduce eddy current losses. A temple arrangement of this kind is advantageous, in particular, because the rotor 2 is accessible in a very simple manner, that is, a container, e.g. a throw away pump, in the interior of which the rotor is arranged, can be inserted in a very simple manner between the winding cores and taken back out.

Figure 8:
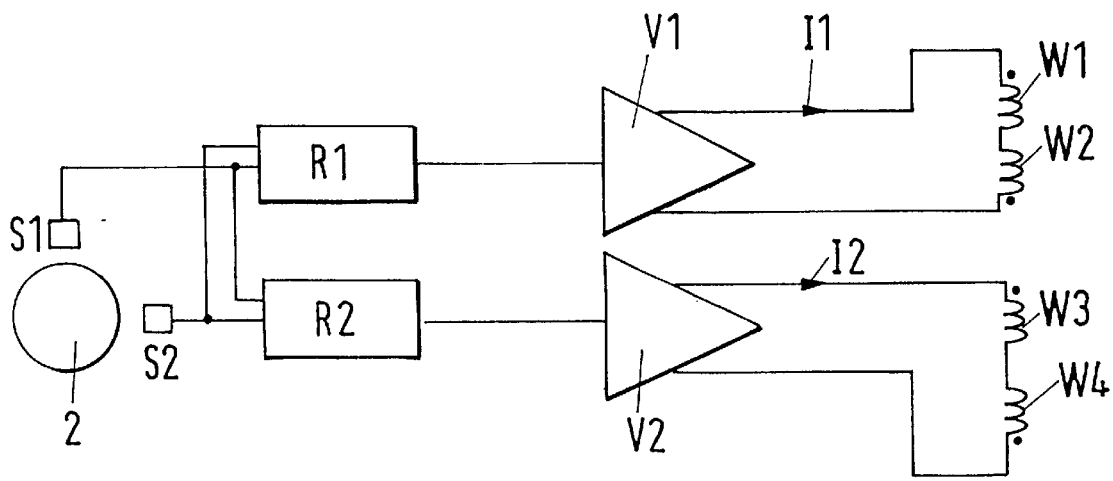
FIG. 8 is a sketch of the principles of a regulation of the position of the rotor.

An electronic control system operating in this manner is schematically represented in FIG. 8; the windings W1, W2 and W3, W4, respectively, are connected in series. The point at the upper or lower end, respectively, of the respective winding Wi, W2 and W3, W4, respectively, stands representatively for the opposite winding sense in each case. One recognizes that the input signals which are produced by the sensors S1 and S2 are fed, in each case, to both control circuits R1 and R2 (e.g. PID regulators) since of course the sensors S1 and S2 in FIG. 7 are arranged in such a manner that a movement of the rotor 2 e.g. towards the sensor S1 must, as a result of the arrangement of the sensor S1, result in both a control current I1 in the windings W1, W2 and a control current I2 in the windings W3, W4 in order to move the rotor 2 back to its desired position. For this, the signals produced by the control circuits R1 and R2 are each fed to a (power) amplifier V1 or V2, respectively, which then impresses the corresponding control current I1 or I2, respectively, into the windings W1, W2 and W3, W4, respectively.

Figure 9:
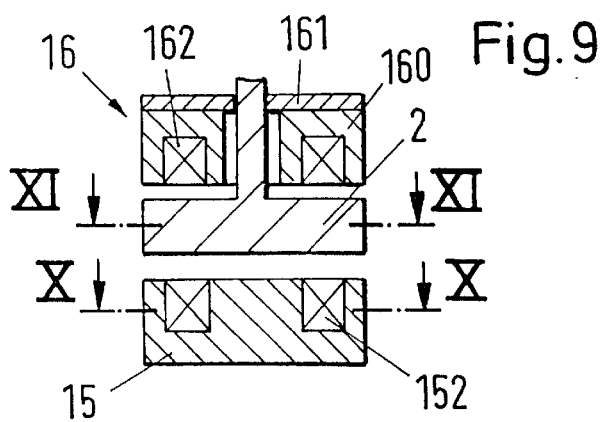
FIG. 9 shows a further exemplary embodiment of a rotational arrangement in accordance with the invention.
Figures 10, 11:
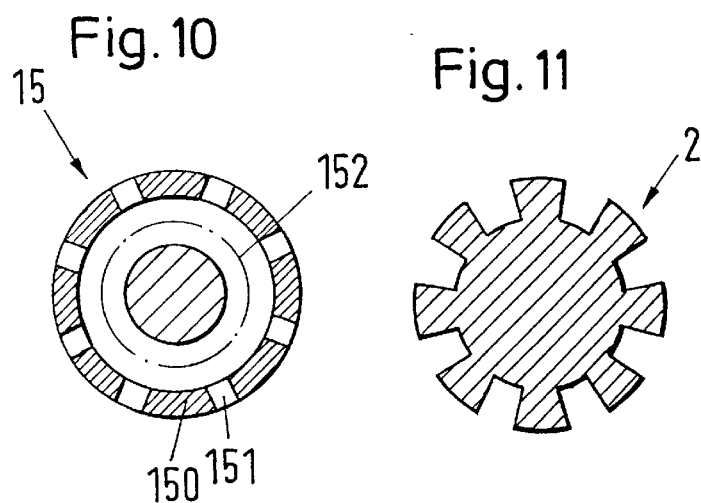
FIG. 10 is a section along the line X—X in FIG. 9.
FIG. 11 is a section along the line XI—XI in FIG. 9.

A further exemplary embodiment of the rotational arrangement in accordance with the invention is illustrated in FIG. 9 in which the bearing stator has a pot core 15 and a stator ring 16. The rotor 2 is arranged between the pot core 15 and the stator ring 16. The pot core 15 has grooves 151 along its periphery as well as teeth 150 between these grooves pointing towards the rotor 2. This can be recognized better in the section of FIG. 10 in which a section along the line X—X in FIG. 9 is illustrated. One recognizes that it is an eight-pole pot core 15 and consequently the stator ring 16 and the rotor 2 must also be designed with eight poles. The rotor can be recognized in FIG. 11, which illustrates a section along the line XI—XI in FIG. 9.

The stator ring 16 has a base disc or base ring 161 with a central aperture for the passage of the rotor shaft and U-shaped "teeth" 160 which point in the direction of the rotor 2 and are formed as U-shaped winding cores. Each of these U-shaped teeth 160 is provided with its own control winding 162, whereas for the pot core 15 in toto a ring winding 152 is laid into the pot core 15. Whereas, however, only a uniform change of the flux over the entire pot core 15 can be produced by the ring winding 152, and thus a tilting of the rotor 2 cannot be corrected, a tilting of the rotor 2 of this kind can be corrected by means of the control windings 162 if, for example, the control windings of four teeth which are arranged to be displaced by 90° are separately excitable.

Alternatively, a further pot magnet can be provided instead of the stator ring 16, e.g. one with a central aperture through which the shaft of the rotor 2 can be led. A ring winding can likewise be laid into a pot magnet of this kind. A tilting of the rotor is however practically not or only with great difficulty correctable in an arrangement of this kind with two pot magnets and in each case only one ring winding per pot magnet.

Figures 12, 13:
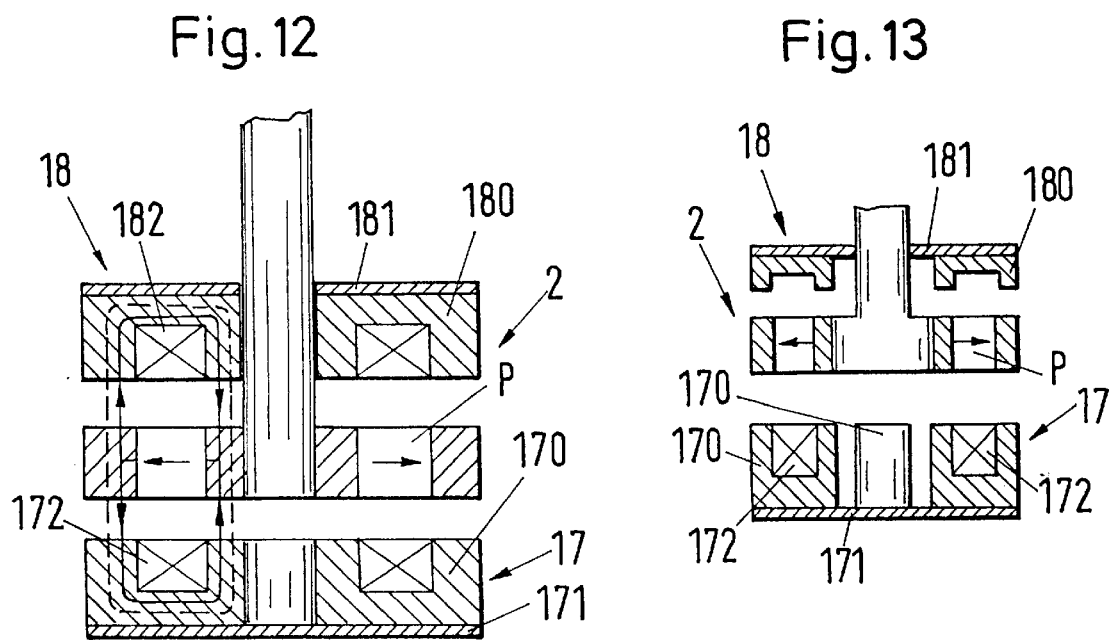
FIG. 12 shows a further exemplary embodiment of a rotational arrangement in accordance with the invention with permanent magnets in the rotor and control windings in both stator rings.
FIG. 13 shows a further exemplary embodiment of a rotational arrangement in accordance with the invention with permanent magnets in the rotor and control windings in only one stator ring.

FIG. 12 shows a further exemplary embodiment of the rotational arrangement in accordance with the invention with two stator rings or, respectively, with a stator disc 17 and a stator ring 18. The stator disc 17 can just as well have a central aperture and thus be formed as a stator ring. Both are made four-poled; they thus have U-shaped teeth 170 and 180, respectively, each of which stands off from the base disc 171 or the base ring 181, respectively, in the direction of the rotor 2 and which is designed as a U-shaped winding core. A control winding 172 or 182, respectively, is wound around each tooth 170 or 180, respectively. The rotor 2 is formed in the shape of a star, likewise of four poles, and has a radially magnetized permanent magnet P in each of its branches.

The path of the permanent magnetic flux (solid line) and the flux produced by the control currents in the control windings 172 and 182, respectively, are easy to recognize. Whereas the permanent magnetic flux is closed to a magnetic circuit through the permanent magnet in each case, this is not the case in the (control) flux produced by the control windings 172 and 182, respectively, because the permanent magnets P themselves have a poor magnetic conductivity so that the flux produced by the control windings 172 and 182, respectively, must in each case close to a magnetic circuit across the air gaps and the respective teeth 170 and 180, respectively. Here also, it can turn out that the control windings 172 and 182, respectively, of teeth 170 or 180, respectively, which lie oppositely with respect to the rotor 2 are connected in series or parallel, yet have a different winding sense. In any case, a tilting of the rotor away from the desired position can also be corrected with an arrangement of this kind.

FIG. 13 represents a variant of FIG. 12 in so far as no control windings are provided in the stator ring 18 in FIG. 13, which is also not necessary in principle, but also produces only a weaker restoring effect on the rotor at the same current strength. In thus far the arrangement in accordance with FIG. 13 is a "skimmed," but therefore also a less complicated and expensive, version of the arrangement of FIG. 12.

Figure 14:
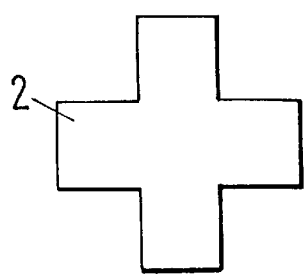
FIG. 14 is a star-shaped rotor with four branches.
Figure 15:
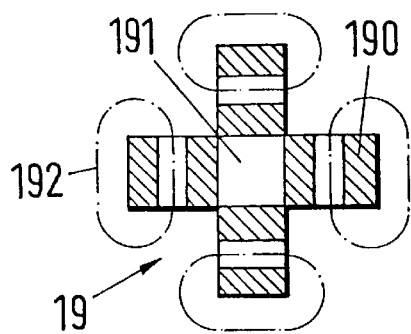
FIG. 15 is a star-shaped stator with U-shaped coil cores for a rotor in accordance with FIG. 14.

FIG. 14 shows an exemplary embodiment of the rotor 2, which is formed in the shape of a star here and is manufactured of a ferromagnetic material (and, similar to the rotor in FIG. 9, comprises no permanent magnets). A possible associated stator ring 19 is shown in FIG. 15. The stator ring 19 or the stator disc, respectively, (here a stator star) has a central star part 191 and U-shaped teeth 190 which are connected to this central star part 191 and which are formed as U-shaped winding coils which are arranged to point toward the branches of the star-shaped rotor 2. A separately excitable control winding 192 is wound about each U-shaped tooth 190. With the help of the separately excitable control windings 192 a tilting of the rotor 2 can be corrected, but a residual flux (bias magnetization) can additionally be produced in addition to a control flux with the help of the control windings 192. It is self explanatory that further (non-illustrated) means must be provided in addition to the stator ring 19 in order to be able to achieve the journalling of the rotor 2 in the desired position (a force equilibrium must of course be present at the rotor in the desired position). Means of this kind are however sufficiently known; for example, a similar stator ring or stator star can be provided which is arranged at the other side of the rotor.

Figure 16:
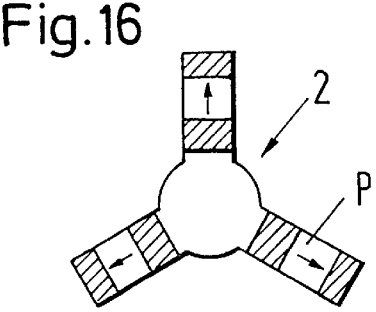
FIG. 16 is a star-shaped rotor with three branches and permanent magnets.
Figure 17:
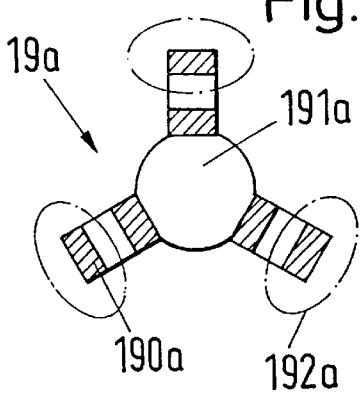
FIG. 17 is a star-shaped stator with three branches and with U-shaped coil cores.

FIG. 16 shows an exemplary embodiment of the rotor 2 which is formed in the shape of a star with a central star part and with three branches which are distributed uniformly over the periphery. Permanent magnets P are arranged in each of the branches. A corresponding stator ring 19a (a three branched stator star) is illustrated in FIG. 17, and the former has a central star part 191a and U-shaped teeth 190a which are connected to this central star part 191a. A separately excitable control winding 192a is wound around each U-shaped tooth 190a so that a tilting of the rotor 2 can be corrected. Here, it is also clear that additional (non-illustrated) means must be present in addition to the control winding in order to effect the journalling of the rotor 2 in the desired position. In principle, only one star-shaped rotor with at least two branches emanating from the central star part is required for the stabilization of a possible tilting of the rotor, but the branches are therein displaced with respect to one another in the peripheral direction by an angle not equal to 180°.

Figure 18:
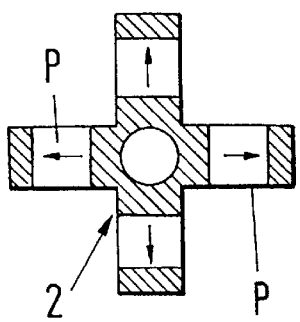
FIG. 18 is a star-shaped rotor with four branches and permanent magnets.
Figure 19:
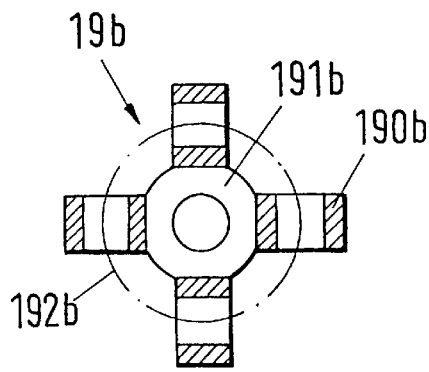
FIG. 19 is a star-shaped stator with four branches, with U-shaped coil cores and with a ring winding.
Figure 20:
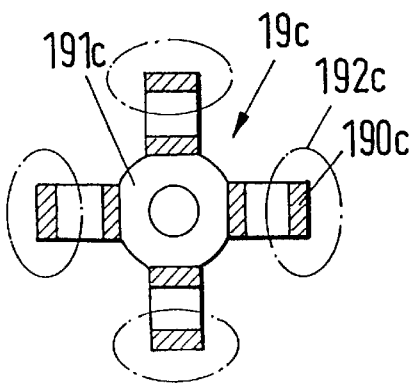
FIG. 20 is a star-shaped stator with four branches, with U-shaped coil cores and with four separate control windings.

Finally, FIG. 18 shows a star-shaped rotor 2 with four branches and permanent magnets P which are arranged therein and are axially magnetized. Possible associated stator rings 19b and 19c, respectively, (four-branched stator stars) are illustrated in FIG. 19 and FIG. 20. Whereas in FIG. 19 the stator ring 19b with the teeth 190b has an inlaid ring winding 192b, by means of which a tilting of the rotor 2 cannot be corrected, an individual, separately excitable control winding 192c is provided around each tooth 190c in the stator ring 19c in FIG. 20, with the help of which a tilting of the rotor 2 can be corrected.

Figure 21:
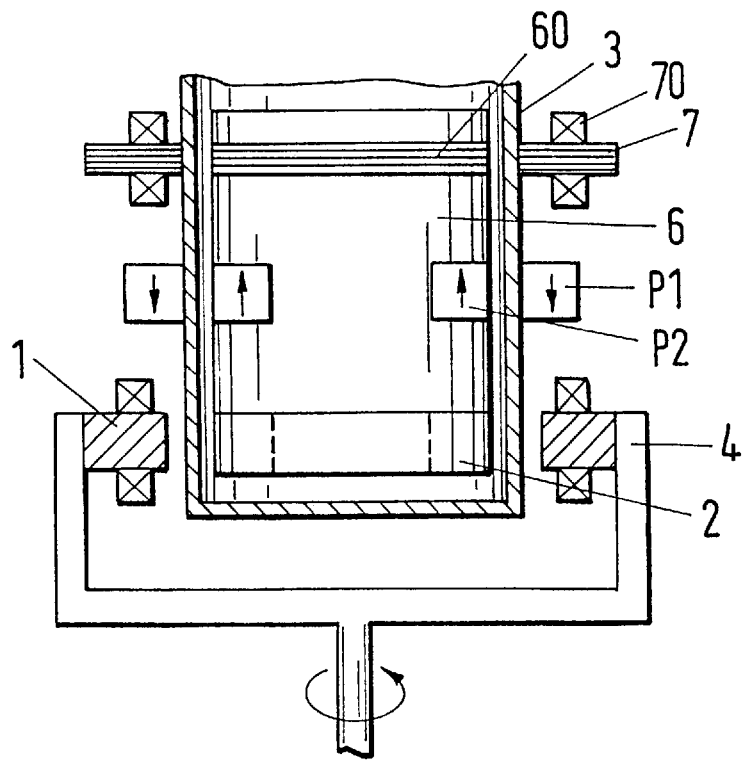
FIG. 21 shows an exemplary embodiment of a use of a rotational arrangement in accordance with the invention with a radial magnetic journalling.

In FIG. 21, use of a rotational arrangement in accordance with the invention is illustrated. One recognizes here a rotor 2 which is connected to a body 6. The rotor 2 and the body 6 which is connected to it are arranged within a vessel 3 which consists of a magnetically poorly conducting material, e.g. of plastic or chrome steel or of a different material which e.g. has particularly advantageous properties with respect to a medium likewise located in the vessel 3.

The magnetic journalling of the rotor 2 and of the body 6 connected to this rotor 2 is done via an upper radial magnetic bearing of a conventional kind, with a laminated ferromagnetic ring 60 being attached to the body 6 which, together with the ring-shaped stator 7 having the stator windings 70, forms the radial magnetic bearing. In this radial magnetic bearing the body 6 is freely rotatable in the bearing plane (i.e. the rotation with respect to the stator is not hindered by reluctance forces); in contrast, however, both a tilting of the body 6 and axial displacement are prevented by reluctance forces. Furthermore, for the prevention of an axial displacement of the body 6, an axial magnetic bearing is provided which comprises two ring-shaped permanent magnets P1 and P2 which are magnetized in the axial direction. The permanent magnets P1 and P2 are arranged at the same level. If now the body 6 is axially deflected from its desired position, then the permanent magnets P1 and P2 exert a passive axial restoring force on the body 6.

Figure 2:
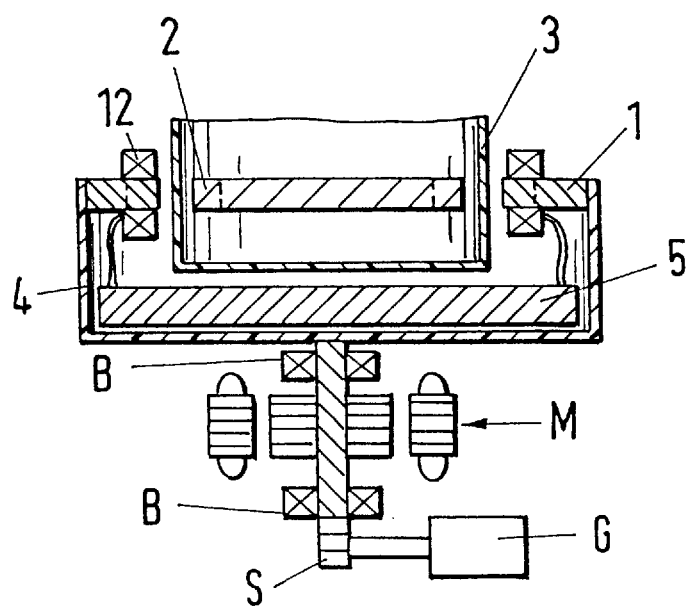
FIG. 2 shows an exemplary embodiment of a rotational arrangement in accordance with the invention.

Finally, a rotational arrangement in accordance with the invention with a stator 1 and a rotor 2 is also provided at the lower end. Here, one is dealing with a radial magnetic bearing as is illustrated in FIG. 1 and FIG. 2 as to its principle. The stator 1 is connected to a rotary bar 4 (see e.g. FIG. 2) which can be driven by a motor. When the rotary bar 4 is driven, and hence when the stator 1 is driven, the rotor 2—as already explained—rotates and thereby the body 6 which is connected to the rotor 2 automatically rotates with it. In contrast to the upper, conventional, radial magnetic bearing, it is thus the case in the lower radial magnetic bearing that not only a tilting and an axial deflection of the rotor 2 are passively prevented, or, respectively, that reluctance forces are exerted, but rather a rotation of the rotor 2 with respect to the stator 1 is also prevented by reluctance forces.

Figure 22:
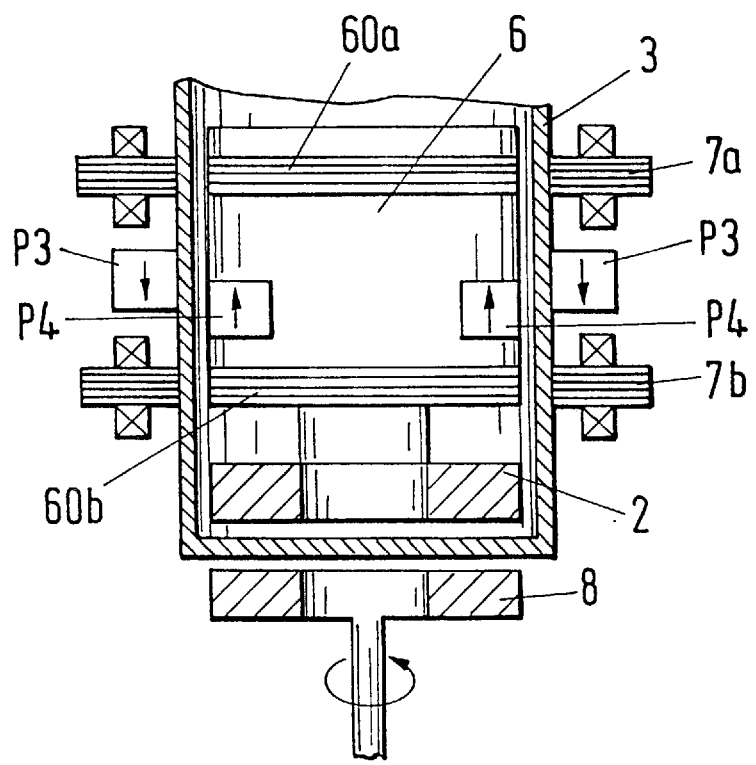
FIG. 22 shows an exemplary embodiment of a use of a rotational arrangement in accordance with the invention with an axial magnetic journalling.

FIG. 22 shows a further use of the rotational arrangement in accordance with the invention (active magnetic journalling). The rotor 2 is connected to the body 6 and both are again arranged within a vessel 3 which consists of a magnetically poorly conducting material. Furthermore, one recognizes two conventional radial magnetic bearings with laminated ring-shaped stators 7a and 7b and with corresponding laminated ferromagnetic rings 60a and 60b which are arranged on the body 6. In these two radial magnetic bearings, the body 6 is again freely rotatable in both bearing planes with respect to the stators, i.e. is not hindered by reluctance forces. In contrast, both an axial deflection of the body 6 away from the desired position and a tilting of the body 6 are impeded by reluctance forces.

Moreover, a further axial bearing is provided. Axially magnetized permanent magnets P3 and P4 are provided, namely, which are arranged to be mutually displaced in the axial direction with respect to one another. The displacement of the permanent magnets P3 and P4 shown in FIG. 22 causes an upwardly directed force to act on the body 6 along with the rotor 2, counter to which, however, a downwardly acting force acts between a stator disc 8 and the rotor 2 so that an equilibrium of forces prevails in the desired position. A rotation of the stator disc 8 produces, via reluctance forces, a rotation of the rotor 2 and thus of the body 6, which of course can rotate unhindered in the bearing plane of the two radial magnetic bearings.

Figure 23:
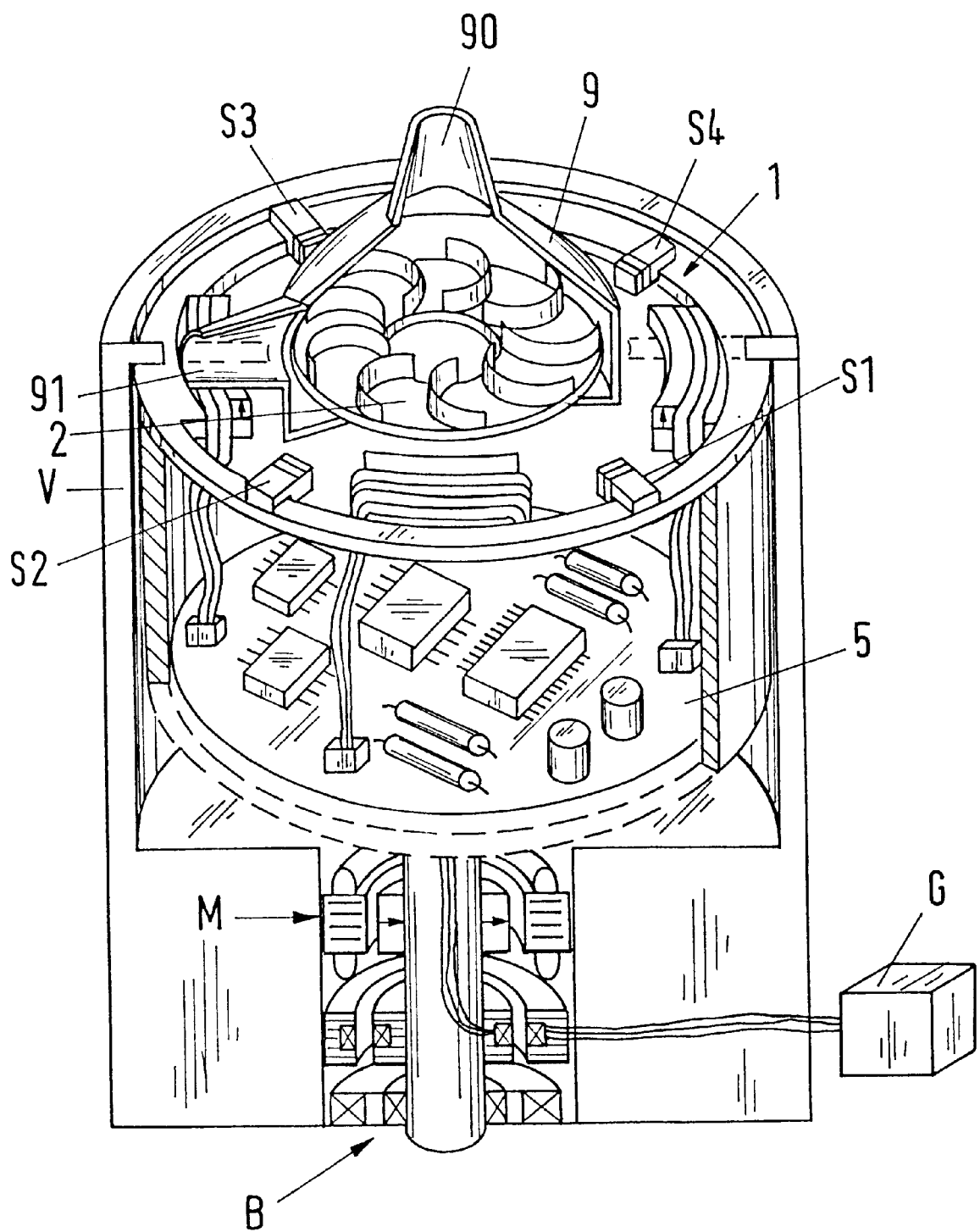
FIG. 23 shows a further exemplary embodiment of a use of a rotational arrangement in accordance with the invention in the form of a pump.

Finally, FIG. 23 shows an exemplary embodiment of a use of the rotational arrangement in accordance with the invention in the form of a pump, in particular a pump for highly pure or biological liquids, especially a blood pump. The pump housing 9 can consist of a material suitable for the transport of blood, e.g. of plastic. The rotor 2 is arranged in the pump housing 9 and has here the form of a vaned wheel (for reasons of drafting no teeth of the rotor are illustrated). The pump housing has an inlet opening 90 and an outlet opening 91, to which in each case an inlet line and an outlet line can be connected. Since a reuse of the parts which have come in contact with blood is out of the question for safety reasons when blood is the liquid to be transported, the parts contacting the blood must practically be kept small in number and, where possible, be uncomplicated and inexpensive in their manufacture. As one can recognize from FIG. 23, the parts contacting the blood are reduced here to the pump housing 9 (plastic part) and the rotor 2 arranged in this pump housing 9. When a pump housing 9 is replaced, the inlet and outlet lines are simply removed and then pushed onto a new pump housing. This pump housing 9 is then inserted into the apparatus V. One recognizes that all other parts of the apparatus V can be reused, for which reason this solution is particularly economical.

The energy supply G, which provides the electrical energy for supplying the electronic control system 5, transfers this energy inductively here. Furthermore, one also recognizes the motor M and a bearing B on the drive side. The control system 5 rotates along with the bearing stator in this exemplary embodiment. It is thereby avoided that a large number of electrical connections from the rotating to the stationary parts are required. The respective position of the rotor 2 is measured with the help of the sensors S1, S2, S3, S4 and communicated to the control system 5, which impresses the corresponding control currents into the control windings when required.

One field of application of the rotational arrangement in accordance with the invention, namely a forwarding apparatus or pump for highly pure or biological liquids, in particular for blood, has already been explained above. The rotational arrangement in accordance with the invention can also be used very well in apparatuses for clean room uses, thus i.e. for blowers for clean room uses or for wafer carriers where it is important that no contamination or gases of any kind from lubricants of mechanical bearings can enter into the clean room. Precisely, this is achieved by the magnetic journalling. But the described magnetically journalled rotational arrangements are also suitable e.g. for stirrers.

Furthermore, it shall be mentioned that in the rotational arrangement in accordance with the invention, in particular, with respect to its use as a blood pump, several aspects from WO-A-96/31934 are conceivable. Thus, both an inner rotor as well as an outer rotor arrangement are conceivable. Furthermore, as already mentioned, a hermetic partition (such as e.g. a motor canning or a vessel) can be arranged between the stator and the rotor. The rotor itself can be encapsulated with a plastic, with a ceramic or with another non metallic material. Furthermore, a ring of electrically well conducting but magnetically poorly conducting material can be provided around the rotor which can serve as a sensor ring for the position measurement by means of eddy current sensors. The determination of the respective angular positions of the rotor can be done by means of Hall sensors, which can likewise serve as position sensors, which is advantageous in the measurement through an electrically conducting motor canning. The rotor, together with the vessel (see e.g. the blood pump described with reference to FIG. 23) surrounding it, can be replaceable and disposable or recyclable in order to be able to guarantee the sterility. More details on all these things can be found in WO-A-96/31934.

Figure 24:
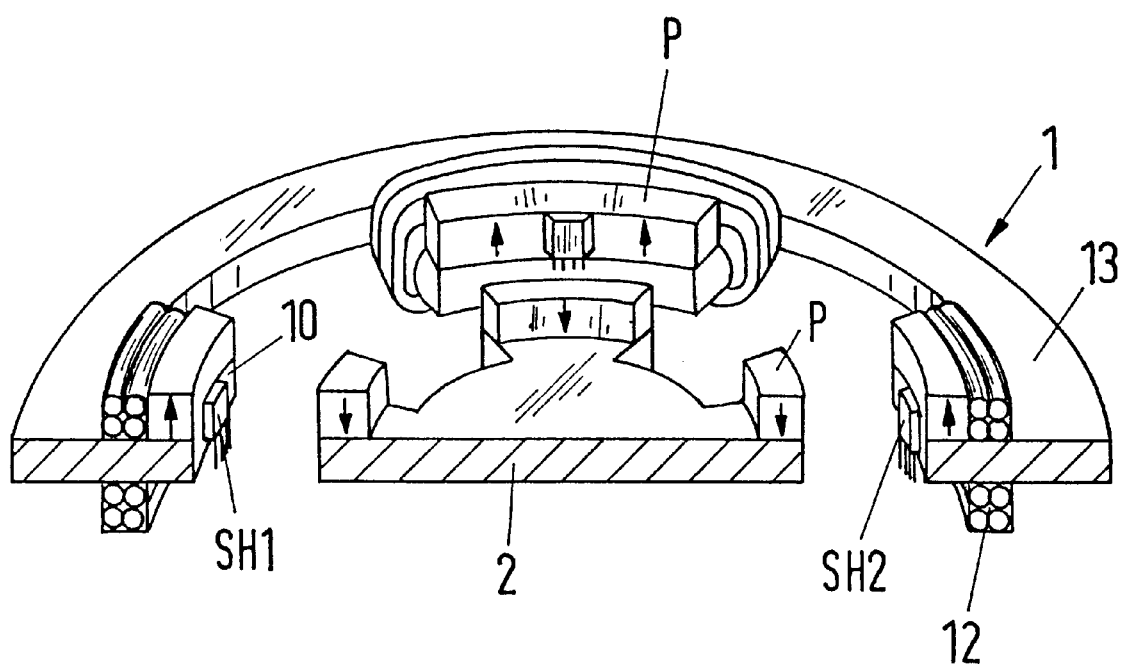
FIG. 24 shows the exemplary embodiment of FIG. 4 with Hall sensors.

In particular the sensor system, in uses in which a vessel 3 (e.g. the pump housing 3 in FIG. 21) is arranged between the stator 1 and the rotor 2, shall once again be discussed because the eddy current sensors which are typically used for the determination of the position of the rotor 2 relatively quickly reach their limits when certain materials (e.g. chrome steel) are used for the vessel 3. Here, magnetic sensors, in particular the already mentioned Hall sensors, prove particularly advantageous. How Hall sensors of this kind can be arranged is shown in the exemplary embodiment of FIG. 24. The exemplary embodiment illustrated there corresponds to the exemplary embodiment of FIG. 4, supplemented, however, by the Hall sensors.

The Hall sensors can be arranged in the air gap between the bearing stator 1 and the rotor 2—as shown with reference to the sensors SH1 and SH2. They can, in particular, also be mounted on (e.g. adhesively fastened to) the teeth 10 of the stator 1. Corresponding sensors are then provided on the other two teeth. The difference of the signals from two geometrically oppositely disposed sensors is particularly suitable for the determination of the position of the rotor 2 in the respective direction even if one sensor per direction would theoretically be sufficient. Alternatively, the Hall sensors can—as shown in an exemplary manner with reference to the sensor SH3—also be attached to the permanent magnets P, and indeed both to the permanent magnets P of the stator 1 as well as to those of the rotor 2, since the stator 1 and the rotor 2 rotate synchronously.

What is claimed is:

1. A magnetically journalled rotational arrangement comprising:

a rotor;

a bearing stator magnetically coupled to the rotor and producing a magnetic journalling of the rotor;

a rotary drive that is associated with the bearing stator; and an electronic control system that is associated with the bearing stator;

wherein the bearing stator is rotatably journalled;

wherein a rotation of the bearing stator produces a rotation of the rotor via the magnetic coupling of the stator to the rotor; and wherein the electronic control system is arranged so as to be rotatable together with the bearing stator.

2. A rotational arrangement in accordance with claim 1 further comprising means for producing reluctance forces that act between the stator and the rotor when the stator is rotated and that result in a synchronous rotation of the rotor with the stator, the means for producing the reluctance forces being provided in the bearing stator and in the rotor.

3. A rotational arrangement in accordance with claim 1 wherein the magnetic journalling of the rotor is designed as a radial magnetic bearing in which two degrees of freedom can be actively regulated while the remaining four degrees of freedom are stabilized via reluctance forces.

4. A rotational arrangement in accordance with claim 3 wherein the two degrees of freedom correspond to the displacement of the rotor in two directions of a bearing plane, and the remaining four degrees of freedom correspond to the axial displacement of the rotor, the rotation of the rotor with respect to the bearing stator and the tilting of the rotor about the two tilt axes.

5. A rotational arrangement in accordance with claim 1 wherein both the bearing stator and the rotor include teeth that point at one another and grooves that are arranged between the teeth of the bearing stator and of the rotor, respectively, with the number and spatial arrangement of the teeth and the grooves of the bearing stator and of the rotor being in agreement.

6. A rotational arrangement in accordance with claim 5 wherein each individual tooth of the teeth of the bearing stator and the rotor that point towards one another have alternating grooves and teeth on their surfaces that point towards one another, with the spatial arrangement of the grooves and the teeth on the surfaces of the individual teeth of the bearing stator and the rotor that point towards one another being in agreement.

7. A rotational arrangement in accordance with claim 5 further comprising control windings in the bearing stator that are associated with the individual teeth of the bearing stator.

8. A rotational arrangement in accordance with claim 7 wherein the bearing stator has a base disc for a base frame and L-shaped winding cores standing off from the base disc or base ring in the axial direction, with shorter limbs of the L-shaped winding cores being arranged to face away from the base disc or the base ring, pointing toward one another and thus forming the teeth of the bearing stator between which the rotor is arranged.

9. A rotational arrangement in accordance with claim 8 wherein the control windings that are provided in the bearing stator are arranged around longer limbs of the L-shaped winding cores.

10. A rotational arrangement in accordance with claim 1 further comprising permanent magnets for the production of a bias magnetization in at least one of the bearing stator and the rotor.

11. A rotational arrangement in accordance with claim 10 wherein the permanent magnets for the production of a bias magnetization are provided only in the bearing stator and not at the rotor.

12. A rotational arrangement in accordance with claim 10 wherein the permanent magnets are provided at both sides of the rotor and in the bearing stator.

13. A rotational arrangement in accordance with claim 10 wherein the permanent magnets are magnetized in one of the axial or the radial direction.

14. A rotational arrangement in accordance with claim 1 wherein the magnetic journalling of the rotor is formed as an axial magnetic bearing in which three degrees of freedom can be actively regulated, and whereas the three remaining degrees of freedom are stabilized via reluctance forces.

15. A rotational arrangement in accordance with claim 14 wherein the three degrees that may be actively regulated correspond to the axial displacement of the rotor and the tilting of the rotor with respect to the two tilt axes, and wherein the three remaining degrees of freedom correspond to the displacement of the rotor in the two directions of the bearing plane and the rotation of the rotor with respect to the bearing stator.

16. A rotational arrangement in accordance with claim 15 wherein the rotor includes a substantially star-shaped form with at least branches going out from a central star part, with permanent magnets that are magnetized in the radial direction being provided in the individual branches.

17. A rotational arrangement in accordance with claim 16 wherein at least three branches that are arranged to be uniformly distributed in a peripheral direction extend out from the central star part.

18. A rotational arrangement in accordance with claim 15 wherein the rotor is formed in the shape of a star with exactly three branches, wherein the bearing stator has a stator star with exactly three branches, with the stator star having U-shaped teeth that point to the branches of the star-shaped rotor and into which in each case a separately excitable control winding is laid.

19. A rotational arrangement in accordance with claim 15 wherein the rotor is formed in the shape of a star with exactly four branches, wherein the bearing stator includes a stator star with exactly four branches, with the stator star having U-shaped teeth that point to the branches of the star-shaped rotor.

20. A rotational arrangement in accordance with claim 19 wherein a separately excitable control winding is laid into the individual U-shaped teeth of the stator star in each case.

21. A rotational arrangement in accordance with claim 15 wherein the bearing stator comprises a pot core that has grooves extending in the radial direction as well as teeth between these grooves that point towards the teeth of the rotor, with a ring winding being laid into the pot core for the production of a bias magnetization, and wherein the bearing stator comprises a ring-shaped winding core that is arranged on the other side of the rotor and that has substantially U-shaped teeth that point in the axial direction toward the rotor and control windings that are laid into the respective U-shaped teeth for the control of the magnetic flux through the individual teeth.

22. A rotational arrangement in accordance with claim 14 wherein the bearing stator includes two stator rings or stator discs, of which in each case one is arranged at one side of the rotor and the other is arranged at the other side of the rotor, with each stator ring or stator disc including U-shaped teeth that are arranged to point towards the branches of the star-shaped rotor and into which control windings are laid.

23. A rotational arrangement in accordance with claim 22 wherein in each case a separately excitable control winding is laid into the U-shaped teeth of only one of the two stator rings or stator discs, wherein one of either no windings or a ring winding is laid into the U-shaped teeth of the other stator ring or stator disc.

24. A forwarding apparatus comprising a rotational arrangement comprising:

a rotor;

a bearing stator magnetically coupled to the rotor and producing a magnetic journalling of the rotor;

a rotary drive that is associated with the bearing stator; and an electronic control system that is associated with the bearing stator;

wherein the bearing stator is rotatably journalled;

wherein a rotation of the bearing stator produces a rotation of the rotor via the magnetic coupling of the stator to the rotor; and wherein the electronic control system is arranged so as to be rotatable together with the bearing stator.

25. A carrier apparatus comprising a rotational arrangement comprising:

a rotor;

a bearing stator magnetically coupled to the rotor and producing a magnetic journalling of the rotor;

a rotary drive that is associated with the bearing stator; and an electronic control system that is associated with the bearing stator;

wherein the bearing stator is rotatably journalled;

wherein a rotation of the bearing stator produces a rotation of the rotor via the magnetic coupling of the stator to the rotor; and wherein the electronic control system is arranged so as to be rotatable together with the bearing stator.

26. A carrier apparatus in accordance with claim 25 wherein the carrier apparatus is a wafer carrier.

27. A blower comprising a rotational arrangement comprising:

a rotor;

a bearing stator magnetically coupled to the rotor and producing a magnetic journalling of the rotor;

a rotary drive that is associated with the bearing stator; and an electronic control system that is associated with the bearing stator;

wherein the bearing stator is rotatably journalled;

wherein a rotation of the bearing stator produces a rotation of the rotor via the magnetic coupling of the stator to the rotor; and wherein the electronic control system is arranged so as to be rotatable together with the bearing stator.

28. A stirrer comprising a rotational arrangement comprising:

a rotor;

a bearing stator magnetically coupled to the rotor and producing a magnetic journalling of the rotor;

a rotary drive that is associated with the bearing stator; and an electronic control system that is associated with the bearing stator;

wherein the bearing stator is rotatably journalled;

wherein a rotation of the bearing stator produces a rotation of the rotor via the magnetic coupling of the stator to the rotor; and wherein the electronic control system is arranged so as to be rotatable together with the bearing stator.

29. A stirrer in accordance with claim 28 wherein the stirrer is a canned motor stirrer.

* * * * *